(12) United States Patent
Strome et al.

(10) Patent No.: US 6,591,140 B2
(45) Date of Patent: Jul. 8, 2003

(54) APPARATUS AND SYSTEM FOR STIMULATING MOUTH MUSCLES

(75) Inventors: Scott E. Strome, Rochester, MN (US); David A. Fabry, Rochester, MN (US); Marshall Strome, Gates Mills, OH (US); Wayne H. Fjerstad, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/737,116

(22) Filed: Dec. 14, 2000

(65) Prior Publication Data

US 2002/0077674 A1 Jun. 20, 2002

(51) Int. Cl.$^7$ ................................................ A61C 1/07
(52) U.S. Cl. ........................ 607/61; 607/134; 606/234
(58) Field of Search ................... 607/61, 134; 606/234, 606/235, 236

(56) References Cited

U.S. PATENT DOCUMENTS

| | | | |
|---|---|---|---|
| 5,544,382 A | * | 8/1996 | Giuliani et al. |
| 5,649,964 A | * | 7/1997 | Berman et al. |
| 5,693,073 A | * | 12/1997 | Glick et al. |
| 5,839,895 A | * | 11/1998 | Fishburne, Jr. |

* cited by examiner

Primary Examiner—Scott M. Getzow
(74) Attorney, Agent, or Firm—Merchant & Gould P.C.

(57) ABSTRACT

An apparatus and system for inducing stimulation of muscles within the mouth. The apparatus includes a housing having a controller. A muscular contact member extends from the housing and is configured to contact muscles within the mouth, including for example the palate and the tongue. A vibrating device cooperates with the controller and muscular contact member to transmit vibration to the muscular contact member and in turn to muscles within the mouth. In the system, such an apparatus is provided that is rechargeable. A storage base receives the rechargeable apparatus when it is not in use and includes a battery charger. The storage base also optionally includes disinfecting means for cleaning the muscular contact member.

20 Claims, 4 Drawing Sheets

APPARATUS AND SYSTEM FOR STIMULATING MOUTH MUSCLES

FIELD OF THE INVENTION

This invention relates generally to devices for the treatment of ear disorders, and more particularly to an apparatus and system for treating eustachian tube dysfunction.

BACKGROUND OF THE INVENTION

Ear infections are a significant problem worldwide. They are typically caused by eustachian tube dysfunction, which prevents adequate aeration of the middle ear space. Pediatric patients are especially prone to this problem due to shorter eustachian tube length, which facilitates bacterial migration, and a decreased angle between the middle ear and the nasopharynx, which prevents proper aeration. Chronic infections can result in decreased hearing and in turn poor speech and language development, or potentially middle ear disease requiring surgical intervention. Chronic ear infections also account for many lost days of work and school. The estimated societal cost for this disease is estimated at $4–5 billion per year in the United States alone.

The current treatment for patients with ear infections ("otitis media") is both medical and surgical. Medical therapy relies primarily on antibiotic use, both for episodes of acute infection and as a long-term prophylactic measure. The implications of long-term antibiotic use are the development of a significant increase in antibiotic resistance, reported as a significant concern in recent studies. Surgical therapy is commonly employed for patients who have failed medical therapy and for patients prone to repeat infections such as those with cleft deformities. Surgery for ear infections relies primarily on the placement of a tube into the middle ear space, which permits adequate aeration. While this technique is highly effective therapy for ear infections, a general anesthetic (with its associated risks) is commonly required in the pediatric population. After the surgery, precautions are required to ensure that fluid or bacteria do not enter the middle ear space through the external auditory canal. Additionally, multiple sets of tubes are often required before a child outgrows their susceptibility to infection.

Despite the prevalence of acute and chronic ear infections, the current treatment methods are essentially limited to antibiotics and surgical tube placement. No treatment to date has successfully focused on direct attempts to correct the physiological problem of inadequate aeration of the middle ear space. Anatomically, the eustachian tube is a cartilaginous structure with dilation controlled by the tensor villi palatine muscle which originates on the eustachian tube and inserts into the midline of the soft palate. When the muscles of the soft palate contract during swallowing, the tensor villi palatine muscle dilates the eustachian tube. Several conditions can prevent such normal eustachian tube opening. However, direct or indirect stimulation of the soft palate can induce eustachian tube dilation and therefore serve as a treatment for ear infections.

Attempts to stimulate the soft palate have relied primarily upon electromuscular stimulation, with electrodes placed in contact with the palate using a device similar to a retainer. Such devices have predominantly been employed for the treatment of snoring and sleep apnea, and have not generated any significant market appeal. This failure is probably due to the fact that the electrical energy required to induce direct palatal stimulation is painful. This makes such an approach a particularly inappropriate one for the pediatric population.

What has been needed is a device that stimulates the muscles of the soft palate comfortably and effectively, thereby reducing or eliminating the need for antibiotic or surgical treatments for ear infections.

SUMMARY OF THE INVENTION

In one aspect of the invention, an apparatus for inducing stimulation of muscles within the mouth comprises a housing, a muscular contact member, a vibrating device, and a controller. The muscular contact member extends from the housing, is for insertion into the mouth, and is configured to contact muscles within the mouth. The vibrating device cooperates with the controller and muscular contact member to transmit vibration to the muscular contact member and in turn to muscles within the mouth.

In another aspect of the invention, a system for inducing stimulation of muscles within the mouth comprises a rechargeable apparatus and a storage base for receiving the rechargeable apparatus. The rechargeable apparatus is for inducing stimulation, and includes a housing having a rechargeable battery. The rechargeable apparatus also includes a vibrating device powered by the battery and a muscular contact member. The vibrating device transmits vibration to the muscular contact member. The storage base receives the rechargeable apparatus when it is not in use, and includes a battery charger for charging the battery.

In another aspect of the invention, a method using an apparatus or system, such as those described above, may be employed to treat various disorders.

These and other advantages and features of novelty which characterize the invention are pointed out with particularity in the claims annexed hereto. However, for a better understanding of the invention and its advantages, reference should be made to the drawings which form a further part hereof, and to the accompanying descriptive matter in which there are illustrated and described preferred embodiments of the invention.

BRIEF DESCRIPTION OF THE FIGURES

Preferred embodiments of the present invention will be described with reference to the accompanying drawings, wherein like reference numerals identify corresponding parts.

DETAILED DESCRIPTION OF THE PREFERRED EMBODIMENTS

Figure 1:
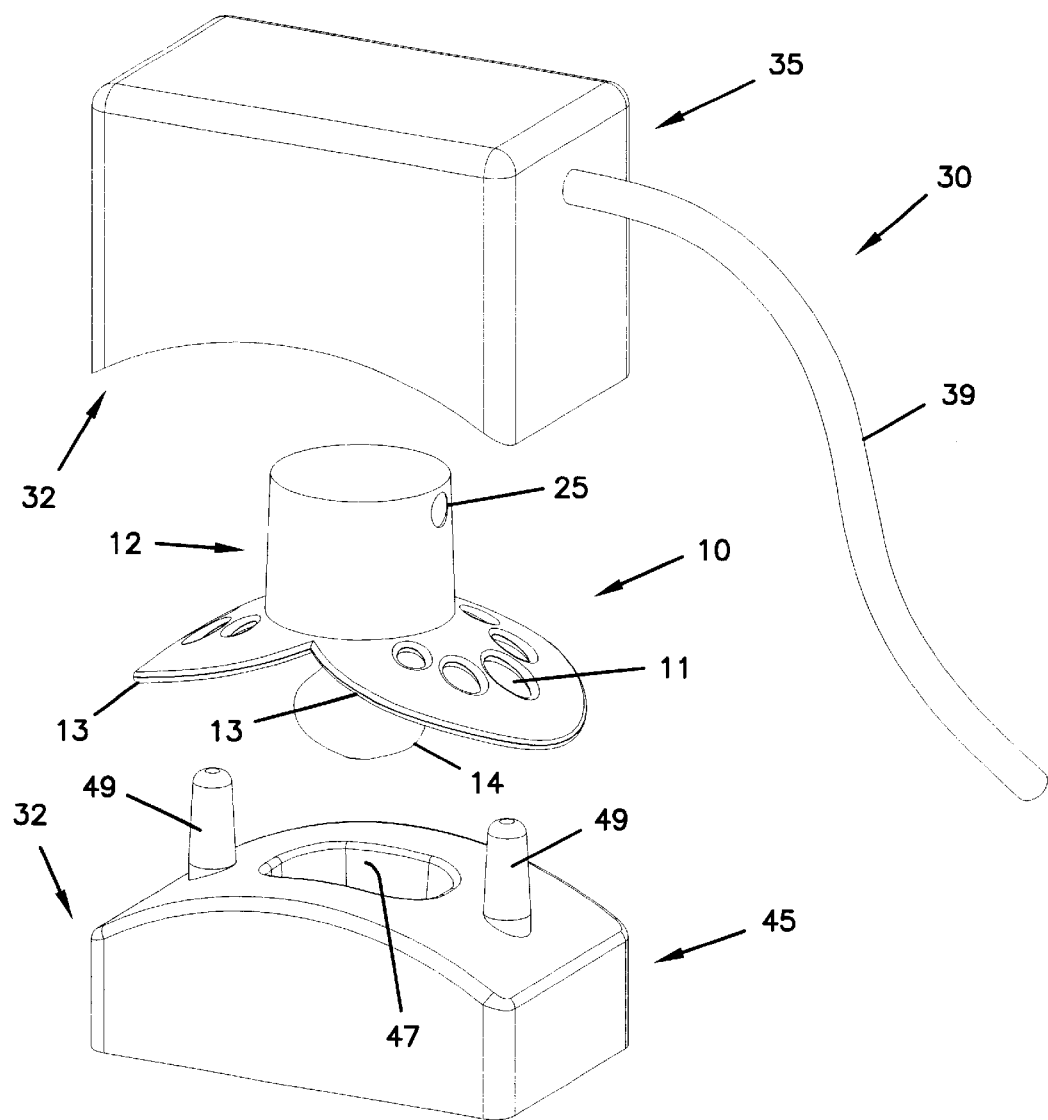
FIG. 1 is an exploded perspective view of an apparatus and system for inducing stimulation of muscles within the mouth, according to the present invention.
Figure 2:
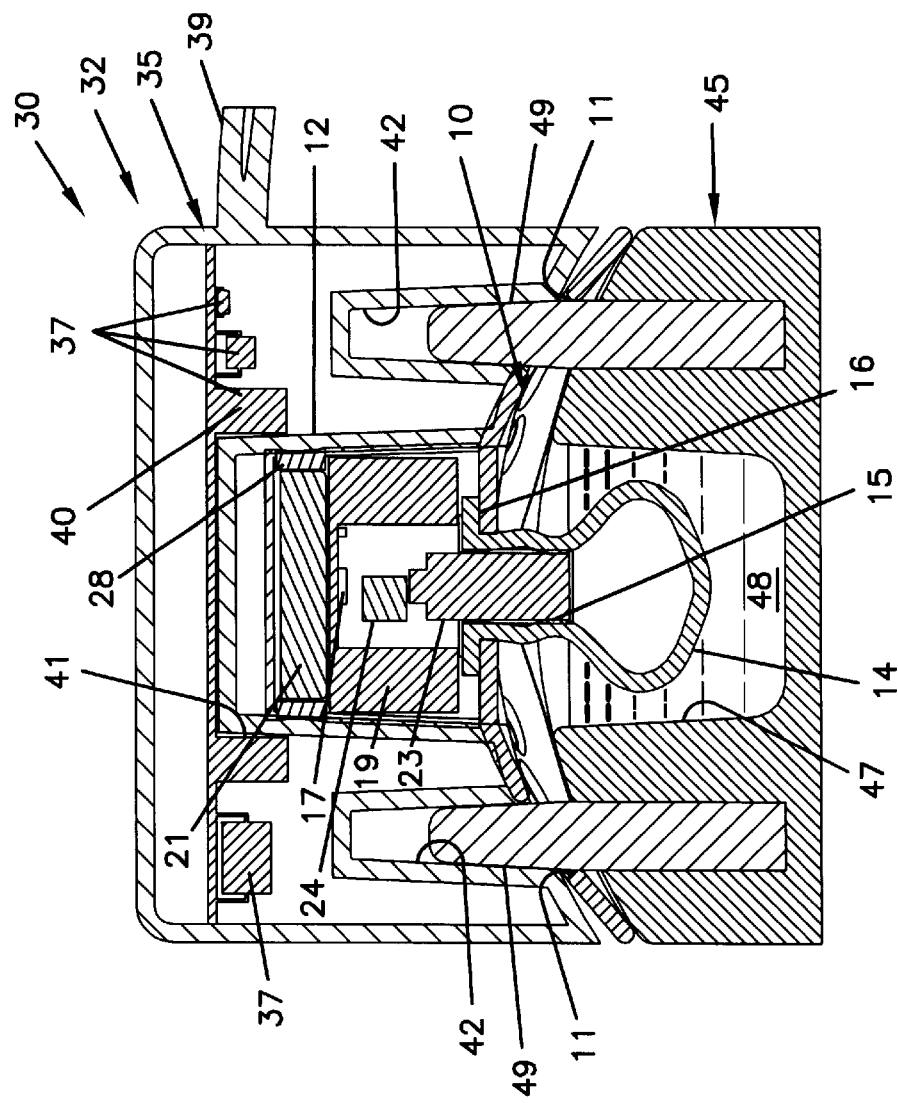
FIG. 2 is an assembled, vertical cross-sectional view of the apparatus and system of FIG. 1.

A preferred embodiment of an apparatus 10 according to the present invention is shown in FIGS. 1 and 2. Apparatus 10 includes housing 12, wings 13 and muscular contact member 14. While apparatus 10 generally, and muscular contact member 14 in particular, are configured like a conventional pacifier and conventional pacifier nipple, respectively, they could be configured in a number of different ways within the principles of the invention. For example, retainer-like or other configurations could be employed that would be suitable for non-pediatric patients.

While the muscular contact member of the preferred embodiment is configured to directly stimulate the soft palate and the base of the tongue (which initiates sucking and swallowing and in turn opens the eustachian tube), other configurations that indirectly induce contraction of the soft palate, including for example ones that stimulate the hard palate or the pharynx could also be employed. Uses of apparatus 10 other than treating ear infection include helping with breast feeding in premature infants, treating colic, and relieving the discomfort associated with airplane descent. The apparatus could also be reconfigured to be more suitable for treatment of snoring, sleep apnea or other disorders.

Within housing 12 are controller 17 and vibrating device 23. Controller 17 activates vibrating device 23 which in turn transmits the vibration to muscular contact member 14 through a physical contact between vibrating device 23 and annular wall 15 (or alternatively two or more walls) of muscular contact member 14. Vibrating device 23 extends from within housing 12 into muscular contact member 14. Flange 16 connects nipple 14 to housing 12. Muscular contact member 14 is preferably made of flexible, elastic material such as latex.

It will be understood that controller 17 and vibrating device 23 could be any of a variety of mechanical or electrical devices. For example, they could comprise a manually wound mechanism.

In the preferred electrical approach, controller 17 is a microprocessor and vibrating device 23 is a vibrating electric motor. Vibrating motor 23 can be for example like that used in a pager, which generates vibration through rotation of an offset counterweight 24. Battery 21, in conjunction with energy storage device 19, powers both microprocessor 17 and vibrating motor 23, as shown in the circuit diagram of FIG. 4. Battery 21 provides power directly to microprocessor 17 and supplies power to energy storage device 19. Energy storage device 19 provides the instantaneous power necessary to power vibrating motor 23 without draining the battery below the power necessary for microcontroller 17. Energy storage device 19 is preferably a storage capacitor such as Dynacap DX545. Resistor R1 is used to limit the current draw from battery 21 to energy storage capacitor 19.

Battery 21 can be disposable or rechargeable. For example, one disposable battery version would be in a single-use apparatus that could be used, for example, on an airplane flight. In the preferred embodiment, battery 21 is a rechargeable battery such as Maxell ML2032.

Figure 3:
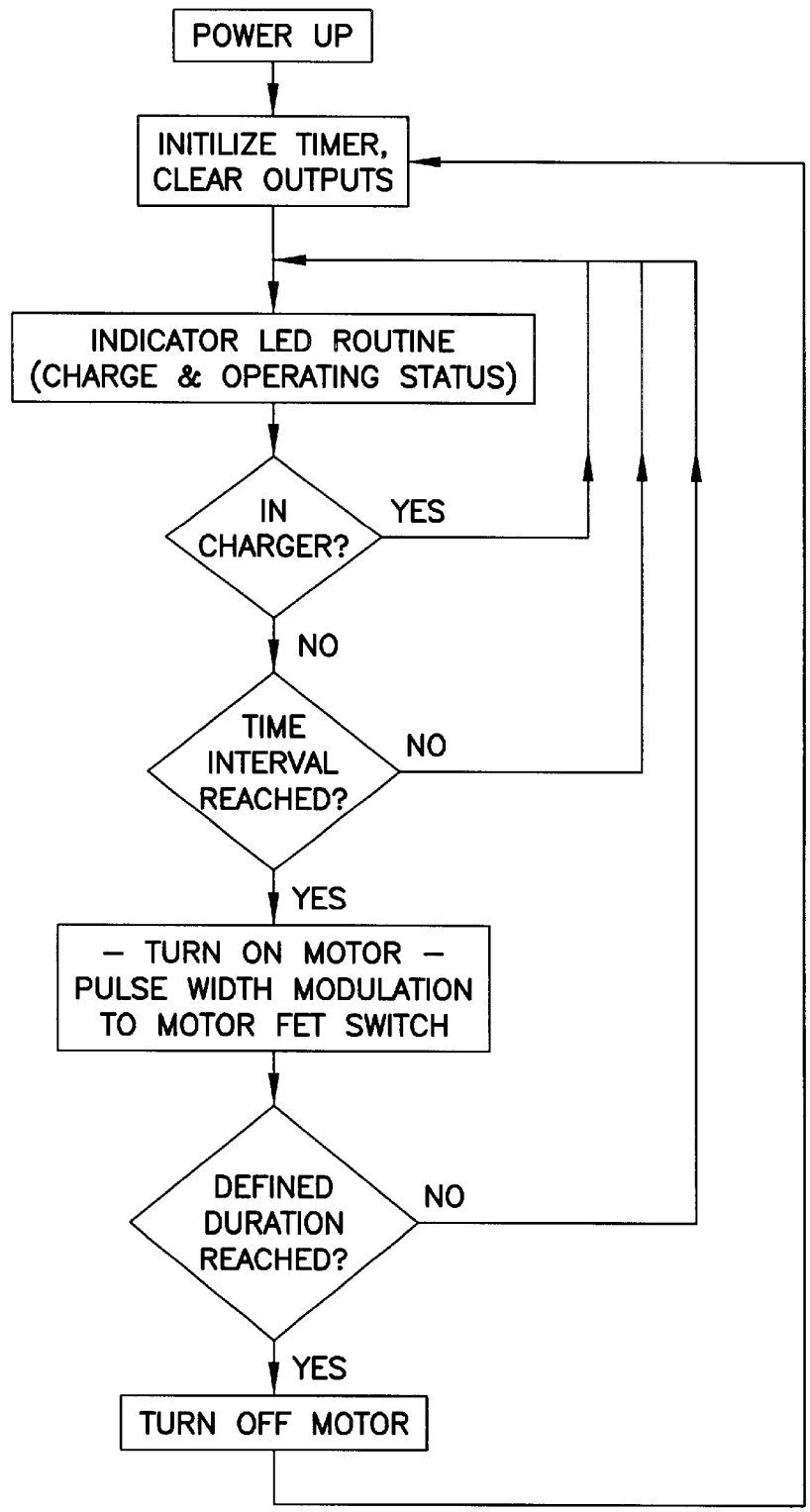
FIG. 3 is a control logic diagram for a system according to the present invention.
Figure 4:
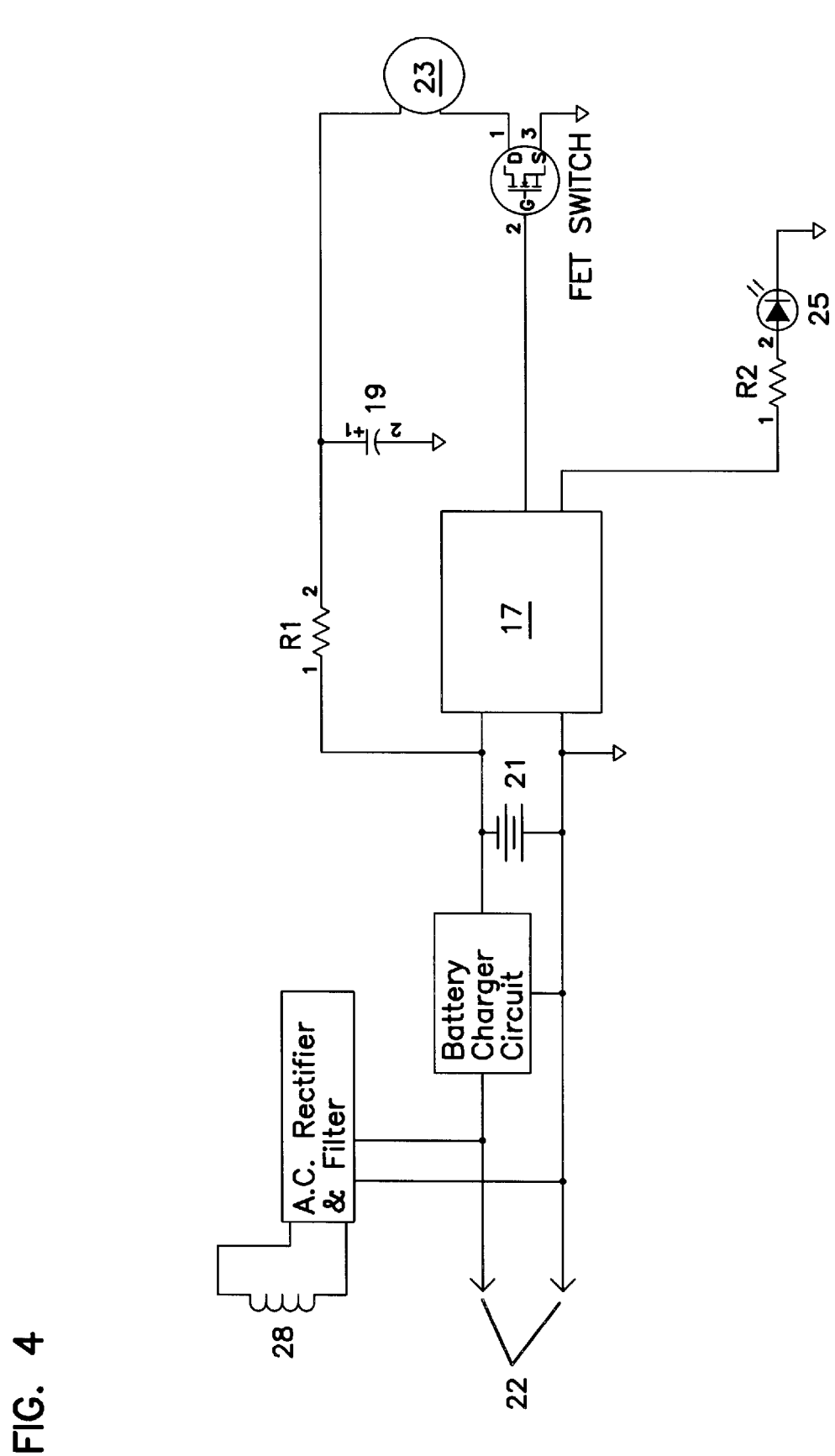
FIG. 4 is an electrical circuit diagram for a system according to the present invention.

The operation of microprocessor 17 is described by the control logic diagram of FIG. 3 and the circuit diagram of FIG. 4. Microcontroller 17 controls the operation of vibrating motor 23 and one or more LED's. Microcontroller 17 can be programmed to start vibrating motor 23 at predetermined time intervals (for example every five minutes). It can also be programmed for the time duration that the motor is energized (for example for ten seconds). A digital output from microcontroller 17 is used as a signal gate to FET switch, which turns on vibrating motor 23. The signal gate of FET switch is a pulse width modulated signal in order to efficiently control the power consumption of vibrating motor 23. A suitable microcontroller is Microchip PIC12C508, and a suitable FET switch is Zetex ZVN3306A.

Apparatus 10 can include one or more LED's 25 (as shown in FIGS. 1 and 4) to provide information about the status of the device. An LED can indicate whether vibrating device 23 is activated (e.g. lighted LED) or whether it is necessary to recharge the battery 21 (e.g. blinking LED). Various other functions and modes can be envisioned for providing the user with information through an LED or other indicating device.

The preferred apparatus 10 is incorporated into a system 30 including storage base 32. Storage base 32 includes charging electronics 37 for recharging battery 21 and therefore apparatus 10. Recharging with an external AC power source (through chord 39) can be accomplished in a variety of ways, with two approaches shown in FIG. 4. One approach is direct contact between corresponding electrical contacts on storage base 32 and apparatus 10, 22. Examples of such battery chargers that would be appropriate are Maxim MAX1679 or MAX1736. Another approach is inductive coupling. Charging electronics 37 in base 32 include an AC excited coil 40 that is inductively coupled to a coil 28 in apparatus 10. The AC signal from coil 28 is rectified and filtered using conventional means to provide power to the battery charger circuit, as shown in FIG. 4.

Storage base includes upper 35 and lower 45 portions. As shown in FIG. 2, apparatus 10 is assembled between portions 35, 45 with positioning prongs 49 extending through openings 11 in apparatus wings 13 and into positioning recesses 42. Housing 12 is retained within cavity 41 of upper portion 35 so as to provide a charging arrangement for either direct electrical contact or inductive coupling as described above.

Electrical charging of an apparatus can be accomplished in other ways as well. For example, the apparatus could be configured to have a plug-in port for connection to a charger. The terms "storage base" and "receives" and variations thereof should be broadly interpreted to include for example such an arrangement.

Storage base 32 can also include a disinfecting chamber 47 for cleaning muscular contact member 14 with disinfectant 48. Disinfectant 48 is preferably a non-toxic cleaning solution that is bacteriostatic and bacteriocidal, such as hydrogen peroxide. It will be understood that, depending on the configuration of muscular contact member 14 specifically and apparatus 10 generally, disinfecting chamber 47 could have a variety of configurations and orientations. Other disinfecting means, such as heat treatment or light, could also be employed within the principles of the invention.

It should be understood that the present invention is not limited to the preferred embodiments discussed above, including with respect to the configuration, arrangement and type of components for example, within the principles of the invention to the full extent indicated by the broad general meanings of the terms in which the appended claims are expressed.

We claim:

1. A system for inducing stimulation of muscles within the mouth, comprising:
   a rechargeable apparatus for inducing stimulation, including a housing having a rechargeable battery, a muscular contact member having a wall with a first wall portion defining a surface that contacts muscles within the mouth and a second wall portion that extends from the housing, and a vibrating device powered by said battery, said vibrating device transmitting vibration to said muscular contact member;
   a storage base that receives said rechargeable apparatus when it is not in use, including a battery charger for charging said battery; and
   a programmable microprocessor in said housing for controlling activation of said vibrating device.

2. A system according to claim 1, wherein said storage base comprises means for disinfecting said muscular contact member.

3. A system according to claim 2, wherein said disinfecting means comprise a disinfecting chamber configured to receive said muscular contact member.

4. A system according to claim 3, wherein said disinfecting chamber comprises a non-toxic cleaning solution.

5. A system according to claim 1, wherein said battery charger is inductively coupled to said battery through corresponding coils in said storage base and in said rechargeable apparatus.

6. A system according to claim 1, wherein said battery charger is electrically connected to said battery through corresponding electrical contacts on said storage base and on said rechargeable apparatus.

7. A system according to claim 1, wherein said storage base comprises two portions between which said apparatus is enclosed.

8. A system according to claim 7, wherein said storage base comprises an upper portion including said battery charger and a lower portion including a disinfecting chamber into which said muscular contact member is inserted.

9. A system according to claim 1, wherein said apparatus is configured generally like a conventional pacifier.

10. A system according to claim 1, wherein said muscular contact member is configured to contact muscles of the soft palate and of the base of the tongue.

11. A system according to claim 1, wherein said vibrating device comprises an electrically powered motor.

12. A system according to claim 1, wherein said microprocessor activates said vibrating device for a defined duration and at defined time intervals.

13. A system according to claim 1, further comprising an indicator in said housing that indicates whether said vibrating device is activated.

14. A system according to claim 1, further comprising an indicator in said housing that indicates the amount of battery life remaining.

15. A system for inducing stimulation of muscles within the mouth, comprising:
  a rechargeable apparatus for inducing stimulation, including a housing having a rechargeable battery, a muscular contact member, and a vibrating device powered by said battery, said vibrating device transmitting vibration to said muscular contact member; and
  a storage base that receives said rechargeable apparatus when it is not in use, including a battery charger for charging said battery;
  wherein said storage base comprises means for disinfecting said muscular contact member.

16. A system for inducing stimulation of muscles within the mouth, comprising:
  a rechargeable apparatus for inducing stimulation, including a housing having a rechargeable battery, a muscular contact member, and a vibrating device powered by said battery, said vibrating device transmitting vibration to said muscular contact member; and
  a storage base that receives said rechargeable apparatus when it is not in use, including a battery charger for charging said battery;
  wherein said storage base comprises two portions between which said apparatus is enclosed.

17. An apparatus for inducing stimulation of muscles within the mouth, comprising:
  a housing having an electrical controller;
  a muscular contact member extending from said housing, for insertion into the mouth, and configured to contact muscles within the mouth, the muscular contact member having a wall with a first portion of the wall defining a surface that contacts muscles within the mouth second portion of the wall extending from the housing;
  a vibrating device cooperating with said controller and muscular contact member to transmit vibration to said muscular contact member and in turn to muscles within the mouth;
  wherein said controller activates said vibrating device for a defined duration and at defined time intervals.

18. An apparatus for inducing stimulation of muscles within the mouth, comprising:
  a housing having an electronic programmable microprocessor as a controller;
  a muscular contact member extending from said housing, for insertion into the mouth, and configured to contact muscles within the mouth, the muscular contact member having a wall with a first portion of the wall defining a surface that contacts muscles within the mouth and a second portion of the wall extending from the housing; and
  a vibrating device cooperating with said controller and muscular contact member to transmit vibration to said muscular contact member and in turn to muscles within the mouth.

19. An apparatus for inducing stimulation of muscles within the mouth, comprising:
  a housing having an controller;
  a muscular contact member extending from said housing, for insertion into the mouth, and configured to contact muscles within the mouth, the muscular contact member having a wall with a first portion of the wall defining a surface that contacts muscles within the mouth and a second portion of the wall extending from the housing;
  a vibrating device cooperating with said controller and muscular contact member to transmit vibration to said muscular contact member and in turn to muscles within the mouth; and
  an indicator that indicates whether said vibrating device is activated.

20. An apparatus for inducing stimulation of muscles within the mouth, comprising:
  a housing having an controller and a battery;
  a muscular contact member extending from said housing, for insertion into the mouth, and configured to contact muscles within the mouth, the muscular contact member having a wall with a first portion of the wall defining a surface that contacts muscles within the mouth and a second portion of the wall extending from the housing;
  a vibrating device cooperating with said controller and muscular contact member, and powered by said battery to transmit vibration to said muscular contact member and in turn to muscles within the mouth; and
  an indicator that indicates the amount of battery life remaining.

* * * * *